United States Patent [19]

Afriat et al.

[11] Patent Number: 5,703,041
[45] Date of Patent: Dec. 30, 1997

[54] STABLE COMPOSITION CONTAINING A WATER-SENSITIVE COSMETIC AND/OR DERMATOLOGICAL ACTIVE AGENT

[75] Inventors: Isabelle Afriat, Paris; Didier Gagnebien, Chatillon, both of France

[73] Assignee: L'Oreal, Paris, France

[21] Appl. No.: 685,845

[22] Filed: Jul. 24, 1996

[30] Foreign Application Priority Data

Jul. 25, 1995 [FR] France ................... 95-09029

[51] Int. Cl.$^6$ ............ A61K 31/69; A61K 38/00; A61K 57/00; A61K 31/59
[52] U.S. Cl. ........... 514/2; 514/64; 514/167; 514/168; 514/401; 514/458; 514/474; 514/588; 514/781; 514/783; 514/859; 514/937; 514/951
[58] Field of Search ............ 514/168, 458, 514/474, 167, 588, 401, 859, 937, 951, 2, 64, 781, 783

[56] References Cited

U.S. PATENT DOCUMENTS

| | | | |
|---|---|---|---|
| 4,711,739 | 12/1987 | Kandathil | 510/284 |
| 5,133,968 | 7/1992 | Nakayama et al. | 424/401 |
| 5,154,916 | 10/1992 | Arraudeau et al. | 424/63 |
| 5,204,093 | 4/1993 | Victor | 424/73 |
| 5,219,561 | 6/1993 | Gagnebein et al. | 424/69 |
| 5,322,683 | 6/1994 | Mackles et al. | 424/45 |
| 5,356,800 | 10/1994 | Jaquess | 435/188 |
| 5,573,768 | 11/1996 | Afriat et al. | 424/401 |

FOREIGN PATENT DOCUMENTS

| | | |
|---|---|---|
| A-1 397 399 | 8/1965 | France . |
| HEI 63 -283213 | 5/1988 | Japan . |
| 61123 | 6/1970 | Luxembourg . |
| 1 255 284 | 6/1970 | United Kingdom . |

OTHER PUBLICATIONS

Chemical Abstracts (106: 143995 w) Yamaguchi et al. (1987).
Chemical Abstracts (109: 156265v) Kinoshita et al. (1988).
Chemical Abstracts (106: 23304 y) Suzuki et al. (1987).
Tzanos, Riv. Ital. Essenze Profumi, Painte, Off. Vol. 59, No. 5, pp. 208–211 (1977) (English Translation).
Masunaga et al, J. Soc. Cosmet. Chem. Jpn., vol. 27, pp. 276–288, (1993) + CA 120:330796h.
CA 112:124943k.
Patent Abstracts of Japan, vol. 13, no. 515 (C–655) [3863], Nov. 17, 1989.

Primary Examiner—Kevin E. Weddington
Attorney, Agent, or Firm—Oblon, Spivak, McClelland, Maier & Neustadt, P. C.

[57] ABSTRACT

A composition for topical application is provided which contains at least one water-sensitive active agent with a topical action and at least one polyol, the latter being present in a quantity which is effective for obtaining a water activity value of the composition of less than or equal to 0.85 with the aim of stabilizing the water-sensitive active agent, the composition containing at least one structuring agent chosen from polymers and oils. The water-sensitive active agent can, in particular, be an enzyme. The composition obtained can be used for cleansing and/or caring for and/or protecting the skin and/or keratinous fibers.

26 Claims, No Drawings

5,703,041

STABLE COMPOSITION CONTAINING A WATER-SENSITIVE COSMETIC AND/OR DERMATOLOGICAL ACTIVE AGENT

BACKGROUND OF THE INVENTION

1. Field of the Invention

The present invention relates to a composition for topical application containing a stabilized active agent, which can be used, in particular, in the cosmetic and/or dermatological fields in order to cleanse and/or care for and/or protect the skin and/or keratinous fibers.

2. Discussion of the Background

It is known to introduce active agents into cosmetic and/or dermatological compositions in order to impart specific treatments to the skin and/or hair, for example in order to cleanse the skin, to combat drying, aging or skin pigmentation, to treat acne or certain skin diseases (eczema, psoriasis), to combat excess weight, to promote the restructuring of the skin or its cell renewal, or to treat seborrhoea of the hair.

It is known, for example, to introduce enzymes into cosmetic compositions, and especially proteases, which are used for their proteolytic properties. These enzymes are sought after in the cosmetic field for their smoothing and cleansing power and their ability to remove dead skin cells.

Unfortunately certain active agents, and in particular those mentioned above, have the disadvantage of being unstable in aqueous media and of being readily degraded or modified under the influence of water. Thus they rapidly lose their activity over time, and this instability goes against the desired efficacy.

Various means have been envisaged for overcoming this disadvantage. In particular, the incorporation of an active agent, especially an enzyme, into a pulverulent composition has been envisaged (see JP-A-63-130514). Moreover, the majority of skin cleansing products containing an enzyme are in this form. It has also been envisaged to use these active agents, and especially enzymes, in a form in which they are immobilized on polymeric supports (see JP-A-61-207499) or in microcapsules (see JP-A-61-254244). Unfortunately, some of these means necessitate a special procedure, which increases the cost and time associated with the preparation of the composition.

Another solution consists in incorporating the active agent into an anhydrous liquid medium (see U.S. Pat. No. 5,322,683). Unfortunately, this solution limits the pharmaceutical form of the composition and does not permit the incorporation of hydrophilic active agents.

There is, therefore, still a need for a composition for topical application containing water-sensitive dermatological and/or cosmetic active agents, in which composition the latter retain all of their properties and, therefore, their efficacy over time.

SUMMARY OF THE INVENTION

It has now been found, unexpectedly, that the use of at least one water-binding polyol in a topical composition containing a water-sensitive active agent, in a quantity which is effective for obtaining a water activity value of the composition of less than or equal to 0.85, and at least one structuring agent, makes it possible to avoid the degradation of the active agent.

DETAILED DESCRIPTION OF THE PREFERRED EMBODIMENTS

The present invention relates to a stable composition for topical application containing at least one water-sensitive active agent with a topical action and at least one polyol, such that the composition contains no calcium salt, in that the polyol is present in a quantity which is effective for obtaining a water activity value of the composition of less than or equal to 0.85, and in that the composition contains at least one structuring agent chosen from polymers and oils.

The invention also relates to a stable composition for topical application containing at least one water-sensitive active agent with a topical action and at least one polyol, such that the polyol is present in a quantity ranging from 40 to 99.99% by weight, relative to the total weight of the composition, and the composition contains at least one structuring agent chosen from acrylic polymers, methacrylic polymers and oils.

It is known that the water content may have an influence on the stability of water-sensitive active agents, but it has never been described nor suggested that the presence of a polyol and a structuring agent might avert the degradation of such active agents. Thus the publication of D. Tzanos (Behavior of enzymes by controlling the medium water activity; Riv. Ital. Essenze, Profumi, Piante Off., Aromi, Saponi, Cosmet., Aerosol, 1977, vol. 59, pages 208–211) teaches the person skilled in the art to use surfactants for the stabilization of enzymes in aqueous media or to attach the enzymes to a porous support. In contrast, it leads the person skilled in the art away from the use of a polyol.

Moreover, U.S. Pat. No. 5,356,800 describes a process for stabilizing enzymes using a mixture containing an alcohol or a glycol, an oxyethylenated alkyldiamine and an amine oxide. According to this patent, enzymes can only be stabilized by using the mixture described.

In addition, JP-A-01-283213 describes a cleansing composition containing an enzyme and a polyol. According to this document, the enzymatic activity is stabilized by addition of a protein such as collagen, elastin or albumin.

FR-A-1397399 describes a process for stabilizing proteases using a mixture of polyol and calcium salt. According to this document, the presence of a calcium salt is indispensable to the stabilization of protease.

Moreover, it is known from the publication J. Soc. Cosm. Chem. Jap., 1993, 27(3), p. 276–288 that it is possible to stabilize proteases by chemically modifying them and that the addition of polyols contributes to improving the stability of the modified protease. According to this publication, chemical modification is necessary to obtain stabilization of the enzymes.

However, it has now been found that, in the case of topical compositions, polyols used in a sufficient quantity and in combination with a structuring agent are able to prevent the degradation of water-sensitive active agents.

The present invention also relates to the use, in a composition for topical application which contains no calcium salt and contains at least one water-sensitive active agent with a topical action, of at least one polyol in a quantity which is effective for obtaining a water activity value of the composition of less than or equal to 0.85, and of at least one structuring agent chosen from polymers and oils, with a view to stabilizing the water-sensitive active agent.

The polymer is preferably chosen from acrylic and methacrylic polymers.

The quantity of the polyol or polyols should preferably be such that the water activity value of the composition is less than or equal to 0.70.

The water activity $a_w$ of a medium containing water is the ratio of the water vapor pressure of the product "$P_{H_2O}$ product" and of the vapor pressure of pure water "$P_{H2O}$ pure" at the same temperature. It can also be expressed as the ratio of the number of molecules of water "$N_{H2O}$" to the total number of molecules "$N_{H2O} + N_{dissolved\ substances}$", which takes into account the molecules of dissolved substances "$N_{dissolved\ substances}$".

The water activity is given by the following formulae:

$$a_w = \frac{P_{H_2O}\ \text{product}}{P_{H_2O}\ \text{pure}} = \frac{N_{H_2O}}{N_{H_2O} + N_{dissolved\ substances}}$$

Various methods can be used for measuring the water activity. The most common is the manometric method, by which the vapor pressure is measured directly.

Conventionally, a cosmetic or dermatological composition has a water activity of about 0.95 to 0.99. A water activity of less than 0.85 represents a considerable reduction in the water activity.

The polyol used according to the invention is chosen, preferably, from glycerol and glycols, preferably poly($C_{2-4}$ alkylene) glycols and glycols containing 3–10 carbon atoms, in particular propylene glycol and polyethylene glycols. Preferred polyethylene glycols have a weight average molecular weight in the range from about 50 to 600.

The quantity of the polyol or polyols to be used is dependent on the type of compositions (gel or emulsion) and on the other constituents of the composition. This quantity must be sufficient to achieve a suitable water activity. The polyol or polyols used according to the invention are preferably present in a quantity of at least 30% by weight, preferably ranging from 40 to 99.99% by weight, and more preferably from 60 to 80% by weight, relative to the total weight of the composition.

According to a preferred embodiment of the invention, the polyol or polyols is or are totally or partially present as a complex with an acrylic or methacrylic polymer. The polymer may also comprise bound water, i.e. can be complexed with a mixture of water and polyol(s).

The term acrylic or methacrylic polymer refers to a homopolymer or copolymer of acrylic or methacrylic acid or a homopolymer or copolymer of an acrylic or methacrylic acid derivative. Preferred acrylic and methacrylic acid derivatives are the esters of these acids with suitable alcohols containing, for example, 1–10 carbon atoms and 1 or more, preferably 1–3 hydroxyl groups. The amount of acrylic or methacrylic acid in the copolymer can be widely varied and is not particularly limiting so long as the properties of the composition of the invention are retained.

The quantity of polymers complexed with the polyol or polyols and, if appropriate, the bound water in the composition according to the invention preferably ranges from 70 to 99.99% by weight, more preferably from 80 to 95% by weight, relative to the total weight of the composition.

As homopolymers which complex water and polyols, those sold under the names NORGEL and LUBRAJEL CG by Guardian may be mentioned. These polymers are glyceryl polyacrylates complexed with more than 65% of glycerol and/or propylene glycol and less than 35% by weight of water. These polymers provide the complexed water and polyol, and may additionally play the part of a gelling agent for the composition.

The comparative tests presented below show that only compositions having a water activity value of no more than 0.85 enable effective retention of the activity of water-sensitive topical active agents and, in particular, of the enzymatic activity of enzymes.

The water-sensitive active agents which can be used according to the invention are, in particular, enzymes (for example lactoperoxidases, lipases, proteases, phospholipases, cellulases), natural extracts such as green tea, balm extract, thyme extract, procyanidolic oligomers (PCOs) such as hawthorn PCO, pine PCO and grapeseed PCO, vitamins, and especially ascorbic acid (vitamin C) and its esters (preferably esters of $C_{1-6}$ alcohols), retinol (vitamin A) and its esters (preferably esters of $C_{1-6}$ alcohols), phosphated and glucosylated vitamins (preferably vitamins A and C), urea and rutin.

The water-sensitive active agent(s) used is (are) advantageously an enzyme, more particularly a protease. This protease can be chosen, for example, from those sold under the trade name SUBTILISIN SP 544 by Novo Nordisk and sold under the trade name LYSOVEG by Laboratoires Sérobiologiques de Nancy.

The quantity of water-sensitive active agent in the composition according to the invention depends on the type of active agent used. In general, the active agent or agents can be used in the composition according to the invention in a quantity ranging from 0.001 to 15% by weight, preferably from 0.01 to 10%, and more preferably from 0.05 to 5% by weight, relative to the total weight of the composition.

As oils which can be used in the invention, mention may be made of mineral oils (liquid petroleum), vegetable oils (jojoba oil), animal oils, synthetic oils (decyl oleate), silicone oils (cyclomethicone, polydimethylsiloxane, dimethicone) and fluorinated oils (perfluoropolyethers). The oil or oils can be present in a quantity ranging from 5 to 60%, preferably from 5 to 40% by weight, relative to the total weight of the composition.

In addition, the composition according to the invention may contain one or more salts whose presence will improve still further the stability of the active agent present therein. Salts which may be mentioned in particular are magnesium salts and sodium salts, and more especially magnesium sulfate, magnesium chloride and sodium chloride. The salt or salts may be present in a quantity ranging from 0.1 to 30%, preferably from 2 to 12% by weight, relative to the total weight of the composition.

The composition according to the invention contains a medium which is topically acceptable, i.e. compatible with the skin and hair, and in particular the composition constitutes compositions for cleansing, protection, treatment or care of the skin and/or hair, in particular for the face, neck, hands, hair, scalp or body, and for the eyelashes.

In addition, a further subject of the invention is the use of the composition according to the invention for cleansing and/or protecting the skin and/or keratinous fibers, i.e. the hair and/or eyelashes.

The present invention also relates to a cleansing composition for the skin and/or the keratinous fibers which contains at least one water-sensitive active agent which has a cleansing action and at least one polyol, such that the composition contains no calcium salt, the polyol is present in a quantity which is effective for obtaining a water activity value of the composition of less than or equal to 0.85, and the composition contains at least one structuring agent chosen from polymers and oils.

Finally, the invention relates to a cosmetic and/or dermatological method of cleansing and/or protecting the skin and/or keratinous fibers, by applying to the skin and/or keratinous fibers a composition which contains no calcium salt and contains at least one water-sensitive active agent which has a topical action, at least one polyol present in a quantity which is effective for obtaining a water activity value of the composition of less than or equal to 0.85 with the aim of stabilizing the water-sensitive active agent, and at least one structuring agent chosen from polymers and oils.

The composition according to the invention can be provided in particular in the form of a solution, a gel, a water-in-oil or oil-in-water emulsion constituting creams, ointments, lotions or milks. This composition may also comprise microcapsules, microparticles or lipid vesicles of ionic and/or nonionic type. These various forms of composition are prepared according to the usual methods.

These compositions constitute, in particular, creams for the protection, treatment or care of the face, hands, feet, body milks for protection or care, lotions, gels or mousses for the care of the skin, mucosae, hair and scalp.

When the composition of the invention is an emulsion, the proportion of the fatty phase may range from 10 to 80% by weight, preferably from 20 to 40% by weight, relative to the total weight of the composition. The emulsion preferably contains at least one dispersant chosen from emulsifiers, vesicles and particles. The oils, the emulsifiers and, if appropriate, the co-emulsifiers used in the composition in emulsion form are chosen from those which are conventionally used in the cosmetic and dermatological fields. The emulsifier and co-emulsifier may be present in the composition in a proportion ranging from 1 to 10% by weight, preferably from 2 to 6% by weight, relative to the total weight of the composition.

In a known manner, the composition of the invention may additionally contain adjuvants which are common in the cosmetic and dermatological fields, such as surfactants, especially foaming surfactants, hydrophilic or lipophilic active agents in addition to water-sensitive active agents, preservatives, antioxidants, solvents, fragrances, fillers, screening agents, odor absorbers and coloring substances. The quantities of these various adjuvants are those which are conventionally used in the fields under consideration, and are for example from 0.01% to 15% of the total weight of the composition. These adjuvants, depending on their nature, can be introduced into the fatty phase, into the aqueous phase and/or into the lipid vesicles.

In addition to the above-mentioned oils, the fatty phase may contain fatty substances such as fatty alcohols, fatty acids (stearic acid), and waxes (silicone wax).

As foaming surfactants which can be used in the invention mention may be made, for example, of disodium cocoamphodiacetate (MIRANOL C2M sold by Rhône-Poulenc) and glucose decyl ether at a concentration of 55% in water (ORAMIX NS10 sold by Seppic). The water content of these raw materials forms part of the total quantity of water in the composition.

As emulsifiers which can be used in the invention mention may be made, for example, of silicone emulsifiers, for instance alkyldimethicone copolyols, such as the cetyldimethicone copolyol sold by Goldschmidt under the name ABIL EM-90, or the mixture of dimethicone copolyol and cyclomethicone sold by Dow Corning under the name 3225C FORMULATION AID.

As hydrophilic active agents it is possible to use, for example, proteins or protein hydrolysates, amino acids, allantoin, sugars and sugar derivatives, and starch.

As lipophilic active agents it is possible to use, for example, tocopherol (vitamin E) and derivatives thereof, essential fatty acids, ceramides and essential oils.

EXAMPLES

Test for stability of enzymatic activity:

The enzymatic activity of an enzyme present in an aqueous gel according to the invention and in two comparative gels was determined using the casein method. According to this method, the casein used as substrate is hydrolysed with the enzyme, liberating amino acids which are subsequently quantified by colorimetry with the aid of Folin-Ciocalteu's reagent. The colorimetric absorbance read off is larger the greater the quantity of enzyme.

The gels tested contained 1% w/w of protease (protease SP 544) and had the following composition:

Gel I (according to the invention): 99% of NORGEL (i.e. 0.99% by weight of acrylic polymer, 66.3% by weight of polyol and 30.7% by weight of water) and 1% by weight of protease.

Gel II (comparative): 99% by weight of propylene glycol alginate with a degree of esterification of 80–85%, at a concentration of 0.5% by weight in water, and 1% by weight protease.

Gel III (comparative): 99% by weight of polysaccharide (FUCOGEL 1000: biosaccharide gum-1 sold by Solabia, based on fucose, galactose and galacturonic acid) and 1% by weight of protease.

The following table gives the results in terms of the percentage enzymatic activity remaining after two months:

| Gel | Water activity of the gel $a_w$ | % enzymatic activity |
|---|---|---|
| Gel I | 0.65 | 71% |
| Gel II | 0.989 | 0% |
| Gel III | 0.967 | 0% |

These results show that only gel I according to the invention allows the enzymatic activity of the protease to be conserved.

The examples which follow of compositions according to the invention are given by way of illustration and are not limiting. The quantities given therein are in % by weight.

Example 1: Gel

| | |
|---|---|
| NORGEL | 85% |
| SUBTILISIN SP 544 | 0.1% |
| Water | up to 100% |

A translucent gel was obtained which can be used as an exfoliating gel. Its water activity was 0.735±0.05.

After 2 months at room temperature, the enzymatic activity of the SUBTILISIN SP 544 was still 80%.

Example 2: Water-in-oil emulsion

| | |
|---|---|
| (a) Aqueous phase: | |
| NORGEL | 71.5% |
| NaCl | 0.5% |
| (b) Oily phase: | |
| Cetyldimethicone copolyol (ABIL EM-90 sold by Goldschmidt) (emulsifier) | 2% |
| Jojoba oil | 4% |
| Polydimethylsiloxane | 8% |
| Liquid petroleum | 10% |
| Decyl oleate | 3.9% |
| SUBTILISIN SP544 | 0.1% |

The procedure for preparing the emulsion was as follows: the aqueous phase was prepared on the one hand and the oily phase on the other hand, and the aqueous phase was emulsified in the oily phase at room temperature with stirring using a homogenizer.

A white cream was obtained which is suitable for facilitating removal of skin cells and for lightening the complexion. Its water activity was 0.62±0.02.

After 2 months at room temperature, the enzymatic activity of the SUBTILISIN SP 544 was still 100%.

Example 3: Cleansing gel

| | |
|---|---|
| SUBTILISIN SP544 | 0.04% |
| NORGEL | 83% |
| MIRANOL C2M (sold by Rhône-Poulenc) | 16% |
| Water | up to 100% |

A foaming cleansing gel was obtained for the face and body which can be rinsed off with water. Its water activity was 0.67±0.02.

Example 4: Cleansing gel

| | |
|---|---|
| NORGEL | 88.97% |
| LYSOVEG | 0.03% |
| ORAMIX NS10 (sold by Seppic) | 11% |

A foaming cleansing gel was obtained for the face and body, which can be rinsed off with water. Its water activity is 0.68±0.02.

Example 5: Water-in-oil emulsion

| | |
|---|---|
| (a) Oily phase: | |
| Dimethicone copolyol and cyclomethicone ("3225C FORMULATION AID" sold by Dow Corning) | 22.6% |
| Dimethicone | 4.9% |
| Mineral oil | 3% |
| (b) Aqueous phase: | |
| Glycerol | 45.5% |
| Magnesium sulfate (stabilizer) | 2% |
| SUBTILISIN SP544 | 0.05% |
| Propylene glycol | 8% |
| Water | up to 100% |

The emulsion was prepared as in Example 2.

A white cream was obtained for smoothing the skin, whose water activity was 0.63±0.02.

After 2 months at room temperature the enzymatic activity of the SUBTILISIN SP 544 was still 90%.

Example 6: Water-in-oil emulsion

| | |
|---|---|
| (a) Oily phase: | |
| Dimethicone copolyol and cyclomethicone ("3225C FORMULATION AID" sold by Dow Corning) | 22.8% |
| Dimethicone | 5% |
| Octyl palmitate | 6.7% |
| Corn starch | 8% |
| Nylon 12 | 5% |
| (b) Aqueous phase: | |
| Glycerol | 8% |
| Propylene glycol | 8% |
| Magnesium chloride | 6% |
| SUBTILISIN SP544 | 0.1% |
| Water | up to 100% |

The emulsion was prepared as in Example 2.

A white cream was obtained for smoothing the skin, whose water activity was 0.75±0.02.

In the above examples it would be possible to replace, according to the invention, the SUBTILISIN SP544 by other enzymes, ascorbic acid, green tea and the other water-sensitive active agents mentioned above.

Obviously, numerous modifications and variations of the present invention are possible in light of the above teachings. It is therefore to be understood that within the scope of the appended claims, the invention may be practiced otherwise than as specifically described herein.

The French priority application no. 95-09029, filed Jul. 25, 1995 is incorporated herein by reference in its entirety.

What is claimed as new and desired to be secured by Letters Patent of the United States is:

1. A composition comprising water, at least one water-sensitive active agent with a topical action and at least one polyol, said composition containing no calcium salt, said polyol being present in a quantity which is effective for obtaining a water activity value of said composition of less than or equal to 0.85, said quantity being at least 30% based on the weight of the total composition, and said composition comprising at least one structuring agent selected from the group consisting of acrylic polymers, methacrylic polymers and oils.

2. The composition of claim 1, wherein said polyol is present in a quantity which is effective for obtaining a water activity value of said composition of less than or equal to 0.70.

3. The composition of claim 1, wherein said structuring agent is a polymer and said polymer is selected from the group consisting of acrylic and methacrylic polymers.

4. The composition of claim 1, wherein said polyol is selected from the group consisting of glycerol and glycols.

5. The composition of claim 1, wherein said structuring agent is an oil and said oil is present in a quantity ranging from 5 to 60% by weight, relative to the total weight of the composition.

6. The composition of claim 5, wherein said oil is selected from the group consisting of mineral oils, vegetable oils, animal oils, synthetic oils, silicone oils and fluorinated oils.

7. The composition of claim 1, wherein said water-sensitive active agent with a topical action is selected from the group consisting of enzymes, natural extracts, procyanidol oligomers, vitamins, phosphated and glucosylated vitamins, urea and rutin.

8. The composition of claim 1, wherein said water-sensitive active agent with a topical action is selected from the group consisting of proteases, green teas, ascorbic acid, retinol and esters thereof.

9. The composition of claim 1, wherein said water-sensitive active agent is present in a concentration ranging from 0.001 to 15% by weight, relative to the total weight of the composition.

10. The composition of claim 1, further comprising a magnesium salt or a sodium salt.

11. The composition of claim 1, further comprising at least one lipophilic or hydrophilic adjuvant selected from the group consisting of preservatives, antioxidants, fragrances, fillers, screening agents, sequestering agents, essential oils, coloring compounds, hydrophilic and lipophilic active agents and lipid vesicles.

12. The composition of claim 1 in the form of an emulsion comprising at least one dispersant selected from the group consisting of emulsifiers, vesicles and particles.

13. The composition of claim 1, wherein said polyol is present in a quantity of 40 to 99.99% by weight based on the weight of the total composition.

14. The composition of claim 1, wherein said polyol is present in a quantity of 60 to 80% by weight based on the weight of the total composition.

15. The composition of claim 3 wherein said polyol is totally or partially present as a complex with a polymer containing polymerized monomers selected from the group consisting of acrylic acid, methacrylic acid and esters of acrylic or methacrylic acid with alcohols containing 1 to 10 carbon atoms and 1 to 3 hydroxyl groups.

16. The composition of claim 15, wherein said complex additionally comprises bound water.

17. The composition of claim 16, wherein said polymer, said polyol and said bound water are present in a quantity ranging from 70 to 99.99% by weight, relative to the total weight of the composition.

18. The composition of claim 1 wherein said water-sensitive active agent is a protease.

19. The composition of claim 1 wherein said water-sensitive active agent is a green tea.

20. The composition of claim 15 wherein said water-sensitive active agent is a protease.

21. The composition of claim 5 wherein said water-sensitive active agent is a protease.

22. The composition of claim 21 wherein said oil is a silicone oil.

23. The composition of claim 1 wherein said water-sensitive active agent is an enzyme.

24. The composition of claim 3 wherein said structuring agent is a glyceryl polyacrylate polymer which is complexed with more than 65% of glycerol, propylene glycol or a mixture thereof, and less than 35% by weight of water.

25. A composition comprising water, at least one water-sensitive active agent with a topical action and at least one polyol, wherein said polyol is present in a quantity ranging from 30 to 99.99% by weight, relative to the total weight of said composition, and said composition comprises at least one structuring agent selected from the group consisting of acrylic polymers, methacrylic polymers and oils.

26. A method of cleansing and/or protecting the skin and/or keratinous fibers, comprising applying the composition of claim 1 to the skin and/or keratinous fibers.

* * * * *